US006998427B2

(12) United States Patent
Del Torto et al.

(10) Patent No.: US 6,998,427 B2
(45) Date of Patent: Feb. 14, 2006

(54) HYDROPHILIC SILICONE ELASTOMER MATERIAL USED IN PARTICULAR FOR TAKING DENTAL IMPRINTS

(75) Inventors: Marco Del Torto, Olona (IT); Yoan Leonard, Leverkusen (DE); Christian Pusineri, Serezin du Rhône (FR)

(73) Assignee: Rhodia Chimie, Boulogne-Billancourt Cedex (FR)

( * ) Notice: Subject to any disclaimer, the term of this patent is extended or adjusted under 35 U.S.C. 154(b) by 0 days.

(21) Appl. No.: 10/480,468

(22) PCT Filed: Jun. 13, 2002

(86) PCT No.: PCT/FR02/02020

§ 371 (c)(1),
(2), (4) Date: Jul. 8, 2004

(87) PCT Pub. No.: WO02/102326

PCT Pub. Date: Dec. 17, 2002

(65) Prior Publication Data

US 2004/0236003 A1     Nov. 25, 2004

(30) Foreign Application Priority Data

Jun. 14, 2001 (FR) ................... 01 07797

(51) Int. Cl.
*C08G 77/08* (2006.01)
(52) U.S. Cl. .................. 523/109; 524/588; 528/15; 528/31
(58) Field of Classification Search .............. 528/15, 528/31; 523/109
See application file for complete search history.

(56) References Cited

U.S. PATENT DOCUMENTS

| 4,778,832 | A | * | 10/1988 | Futami et al. | ............... 523/109 |
| 6,121,362 | A | * | 9/2000 | Wanek et al. | ............... 524/448 |
| 6,291,546 | B1 | * | 9/2001 | Kamohara et al. | ......... 523/109 |
| 6,677,393 | B1 | * | 1/2004 | Zech et al. | ................ 524/366 |
| 6,762,242 | B1 | * | 7/2004 | Torto et al. | ................ 524/588 |
| 6,861,457 | B1 | * | 3/2005 | Kamohara | ................ 523/109 |

FOREIGN PATENT DOCUMENTS

| EP | 0 480 238 A | 4/1992 |
| FR | 2 791 996 A | 10/2000 |
| GB | 2 314 849 A | 1/1998 |
| GB | 2 337 524 A | 11/1999 |

* cited by examiner

*Primary Examiner*—Margaret G. Moore
(74) *Attorney, Agent, or Firm*—Buchanan Ingersoll, P.C

(57) ABSTRACT

A crosslinkable silicone material made of a silicone elastomer by polyaddition reaction is provided. The crosslinkable silicone material is especially useful for taking impressions such as, for example, dental impressions.

20 Claims, 1 Drawing Sheet

HYDROPHILIC SILICONE ELASTOMER MATERIAL USED IN PARTICULAR FOR TAKING DENTAL IMPRINTS

The field of the present invention is that of the silicone materials comprising a polyorganosiloxane (POS for short) composition, which can be crosslinked or cured into a silicone elastomer by polyaddition reactions, and a wetting agent allowing a hydrophilic character to be conferred on the said material. The applications intended for such systems are, especially, the taking of impressions and, more particularly, the taking of dental impressions within the context of producing dentures. The expression "taking of impressions" is understood to mean, in the present text, not only the operations of taking impressions of whatever object and of whatever shape, in order to produce a model made in particular of plaster, but also the operations of reproducing or duplicating models made in particular of plaster. The expression "taking of dental impressions" is understood to mean, in the present text, not only the operations in which dental impressions are taken in the mouth in order to obtain precise copies or jaws or parts of jaws which may or may not bear, totally or partly, teeth and to form plaster models, but also the duplicating operations in which plaster models of jaws or parts of jaws are reproduced in a laboratory for dentures. The intended applications also encompass the manufacture of moulded parts, other than duplicates in dental applications, which are capable of developing a pronounced hydrophilic and/or antistatic character on the surface.

The subject of the present invention is also a process for preparing the hydrophilic silicone elastomer material. The subject of the invention is also the use of the said material for taking impressions, for example dental impressions and for the manufacture of moulded parts, other than duplicates in dental applications, which are capable of developing a pronounced hydrophilic and/or antistatic character on the surface.

Figure 1:
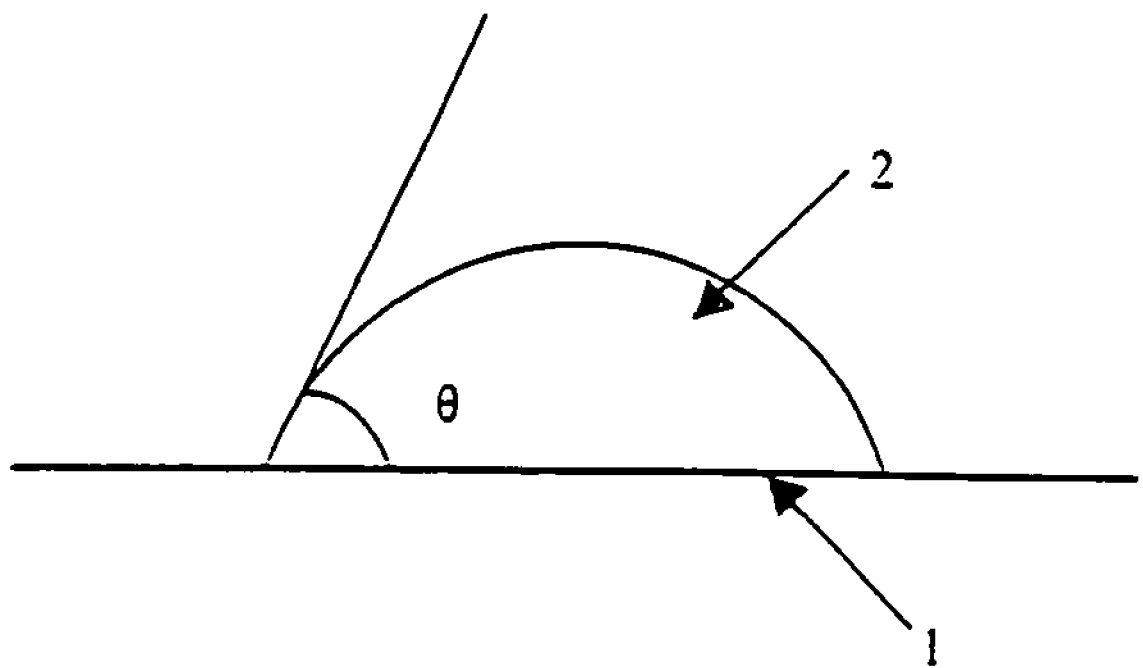
FIG. 1 is a schematic showing a contact angle ($\Theta$) between a water drop and a deposition surface of a crosslinked silicone film.

Silicone materials are widely used in these fields. This is partly due to the fact that silicone materials exhibit, on the one hand, a great diversity of chemical, mechanical and physical characteristics and, on the other hand, non-toxic, non-irritant and non-allergenic behaviour. Furthermore, silicone materials constitute poor substrates for the cultivation of microorganisms, thereby giving them remarkable properties with regard to hygiene.

The POS compositions of interest within the context of the present invention comprise at least:
- a POS(1) composition carrying Si-alkenyl functional groups which are capable of reacting by addition reactions with the Si—H crosslinking functional groups of a POS(2) composition;
- a POS(2) composition carrying Si—H functional groups which are capable of reacting with the Si-alkenyl functional groups of the POS(1) composition;
- optionally, an unreactive POS(3) composition, differing from the POS(1) and POS(2) compositions, which can be used as a diluent;
- a catalyst for catalysing the polyaddition reactions; and
- a particulate reinforcing mineral filler and optionally a semi-reinforcing or bulking filler.

It is known that such POS compositions, which advantageously may be in the form of two components, are crosslinkable or curable at room temperature and are particularly beneficial in the field of taking impressions, in particular dental impressions, since these compositions are endowed with flow and film-forming properties before crosslinking, making it possible to take an impression of whatever shape with excellent reproduction of the details. Moreover, these compositions can crosslink by polyaddition reactions in a few minutes at room temperature; in addition, they are non-toxic and satisfy the European pharmaceutical regulations. The crosslinking, which results in the hardening of the silicone composition, makes it possible to form moulds made of elastomers having mechanical properties, dimensional stability and thermal resistance which all comply with the desired specifications.

However, compositions for impressions based on silicone crosslinking by polyaddition reactions are intrinsically hydrophobic. Thus, when the mixed moulding compound is applied to the wet surface of teeth and gums, there may therefore be a casting defect or insufficient penetration into the hollows of the gums because of the presence of liquid residues; after crosslinking, the reproduction is therefore defective. Moreover, during the operations of duplicating the positive of the plaster impression, refractory plaster of hydrophilic character has to be poured into a mould made of hydrophobic silicone; there may be occlusion of small air bubbles because of the incompatibility between the surfaces, this occlusion resulting in defective reproduction.

These drawbacks may be practically eliminated by giving the intrinsically hydrophobic POS compositions a hydrophilic character by the use of various surfactants; thus, it has been proposed to use: in U.S. Pat. No. 4,657,959, a polyorganosiloxane with polyether functional groups; in U.S. Pat. No. 4,691,039 and U.S. Pat. No. 4,752,633, an ethoxylated silane; in U.S. Pat. No. 5,064,891, a polyorganosiloxane with polyol functional groups; in EP-A-0,480,233, a poly(alkoxylated) fatty alcohol; and, in FR-A-2,600,886, a water-soluble protein combined if necessary with a nonionic surfactant.

The hydrophilic character is quantified by measuring the contact angle of drops of water which are deposited on the surface of crosslinked films, 2 mm in thickness, made from a POS polyaddition composition. The angle is measured 3 minutes after the water drops have been deposited. In FIG. 1 appended hereto, the reference 1 represents the surface of the crosslinked silicone film, the reference 2 represents the water drop deposited on the said surface and the symbol $\theta$ represents the contact angle between the drop and the deposition surface, which angle is measured.

In the absence of a surfactant, the contact angles are generally around 100 to 105°. The surfactants, which are incorporated into the POS polyaddition composition, give the said compositions, and the crosslinked silicone elastomers which stem therefrom; a hydrophilic character which is manifested in a reduction in the value of the contact angles of drops of water deposited on the surface of the crosslinked elastomers. To be able to be regarded as hydrophilic, the POS polyaddition composition must have contact angles of less than 65°.

Within such a technical context, one of the essential objectives of the present invention is to provide a silicone that can be used especially for taking impressions, for example dental impressions, which makes it possible to achieve, after crosslinking, contact angles:
  equal to or less than 40°;

with the possibility of achieving values equal to or less than 30°; and better still with the possibility of achieving, as required, values as low as those ranging from 25 to 27°.

To achieve this objective, among others, the inventors have surprisingly and unexpectedly discovered the beneficial use of a carefully selected wetting agent, consisting of particular nonionic surfactants and in synergistic combinations of particular nonionic surfactants.

More precisely, the present invention, according to its first subject-matter, relates to a silicone material, usable especially for taking impressions, for example dental impressions, which comprises the following constituents:

I. a POS composition crosslinkable by polyaddition reactions comprising:
  (1) at least one POS composition carrying Si-alkenyl functional groups which are capable of reacting by addition reactions with the Si—H crosslinking functional groups of a POS(2) composition,
  (2) at least one POS composition carrying Si—H functional groups which are capable of reacting with the Si-alkenyl functional groups of the POS(1) composition,
  (3) optionally, at least one unreactive POS composition, differing from the POS(1) and POS(2) compositions, which can be used as a diluent,
  (4) a catalyst for catalysing the polyaddition reactions,
  (5) a particulate reinforcing mineral filler;

II. a wetting agent consisting of one or more surfactants allowing the surface of the silicone material to be given a pronounced hydrophilic character, both before and after crosslinking;

the said silicone material being characterized in that the wetting agent II is chosen from the group consisting of:
  (a) at least one nonionic surfactant consisting of an ester obtained by esterification of a saturated monocarboxylic acid having a $C_{10}$–$C_{14}$ linear or branched chain by a poly(oxyalkylene) glycol containing a number of alkoxylated units such that the molar mass $M_w$ of the ester lies within the 400 to 800 g/mol range, the HLB of the said surfactant or of the mixture of surfactants ranging from 6 to 14;
  a synergistic combination (a)+(b), where (b) denotes at least one nonionic surfactant consisting of a polyalkoxylated saturated aliphatic alcohol having a $C_5$–$C_{16}$ linear or branched chain, containing a number of alkoxylated units such that the molar mass $M_w$ of the polyalkoxylated alcohol lies within the 200 to 1400 g/mol range, the HLB of the said surfactant (b) or of the mixture of surfactants (b) ranging from 6 to 16; and
  a synergistic combination (b1)+(b2), where (b1) denotes at least one nonionic surfactant consisting of a polyethoxylated saturated aliphatic alcohol having a $C_{10}$–$C_{16}$ linear or branched chain, containing from 6 to 10 ethylene oxide (EO) units, the HLB of the said surfactant (b1) or of the mixture of surfactants (b1) ranging from 12 to 16, and (b2) denotes at least one nonionic surfactant consisting of a polyalkoxylated saturated aliphatic alcohol having a $C_6$–$C_{13}$ linear or branched chain, containing a number of ethylene oxide (EO) and propylene oxide (PO) units such that the molar mass $M_w$ of the polyalkoxylated alcohol lies within the 500 to 1200 g/mol range, the HLB of the said surfactant (b2) or of the mixture of surfactants (b2) ranging from 6 to 16.

In general, the amount of surfactant or that of a mixture of surfactants, expressed in % by weight with respect to the total mass of the POS I composition, is equal to or greater than 1% and preferably lies within the 1.2 to 4% range, and more preferably still lies within the 1.2 to 3% range.

A procedure for implementing the present invention, which is preferred in order to achieve contact angles equal to or less than 40° (procedure 1), is the use, in the amounts given above, of a wetting agent chosen from the group consisting of:
  (a1) at least one nonionic surfactant consisting of an ester obtained by esterification of a saturated monocarboxylic acid having a $C_{10}$–$C_{14}$ linear or branched chain by a poly(oxyalkylene) glycol containing from 7 to 11 EO and/or PO units, the HLB of the said surfactant or of the mixture of surfactants ranging from 10 to 14;
  a synergistic combination (a1)+(b1);
  a synergistic combination (a1)+(b2);
  a synergistic combination (a1)+(b3), where (b3) denotes at least one nonionic surfactant consisting of a polyethoxylated saturated aliphatic alcohol having a $C_{10}$–$C_{14}$ linear or branched chain, containing from 1 to 4 EO units, the HLB of the said surfactant (b3) or of the mixture of surfactants (b3) ranging from 6 to 10; and
  a synergistic combination (b1)+(b2).

As specific examples of surfactants, mention may particularly be made of the following compounds:

(a)–(a1):
  an ester obtained by esterification of a $C_{13}$ fatty acid (lauric acid) by a poly(oxyethylene) glycol containing about 9 EO units, having an HLB of 13.1, sold under the name LINCOL PE 400 ML (abbreviated to TA1);

(b)–(b1):
  a polyethoxylated $C_{13}$ saturated aliphatic alcohol containing about 8 EO units, having an HLB of 12.8, sold under the name RHODASURF ROX (abbreviated to TA2);

(b)–(b2):
  a polyalkoxylated $C_8$ saturated aliphatic alcohol containing a number of EO and PO units such that the molecular mass $M_w$ of the polyalkoxylated alcohol is equal to about 1000 g/mol, sold under the name TEGOPREN LP 111 (abbreviated to TA3);
  a polyalkoxylated $C_{10}$–$C_{12}$ saturated aliphatic alcohol containing about 4 EO units and 3 PO units, having an HLB of 7, sold under the name ANTAROX FM 33 (abbreviated to TA4); and (b)–(b3):
  a polyethoxylated $C_{12}$ saturated aliphatic alcohol containing about 2 EO units, having an HLB of 8.1, sold under the name RHODASURF OT/2 (abbreviated to TA5).

A procedure for implementing the present invention which is especially suitable for achieving contact angles equal to or less than 30° (procedure 2) is the use of a wetting agent chosen from the group formed by:
  a synergistic combination (a1)+(b1);
  a synergistic combination (a1)+(b2); and
  a synergistic combination (b1)+(b2); where:
  the amount of the surfactant mixture lies within the 1.2 to 3% range;
  the (a1)/(b1) weight ratio lies within the 0.5 to 1.5 range;
  the (a1)/(b2) weight ratio lies within the 0.5 to 7 range with the three conditions whereby: (i) when the said ratio lies within the 0.5 to 1.2 range, then the amount of the surfactant mixture is less than 1.8%; (2i) when the said ratio lies within the 3 to 7 range, then the amount of the surfactant mixture is equal to or greater than 1.8%; and (3i) when the said ratio lies within the range going from a value greater than 1.2 to a value less than 3, then the amount of the surfactant mixture is equal to any value taken within the 1.2 to 3% range given above;

the (b1)/(b2) weight ratio lies within the 0.5 to 1.5 range.

A procedure for implementing the present invention which is especially suitable for achieving contact angle values as low as those ranging from 25 to 27° (procedure 3) is the use of a wetting agent consisting of a synergistic combination (a1)+(b2), where:

the amount of the surfactant mixture lies within the 1.2 to 3% range;

the (a1)/(b2) weight ratio lies within the 0.7 to 1.7 range, with the three conditions whereby: (i) when the said ratio lies within the 0.7 to 1 range, then the amount of the surfactant mixture is less than 1.8%; (2i) when the said ratio lies within the 1.5 to 1.7 range, then the amount of the surfactant mixture is equal to or greater than 1.8%; and (3i) when the said ratio lies within the range going from a value greater than 1 to a value less than 1.5, then the amount of the surfactant mixture is equal to any value taken within the 1.2 to 3% range given above.

Another procedure for implementing the present invention which is especially suitable for achieving contact angle values as low as those ranging from 25 to 27° (procedure 4) is the use of a wetting agent consisting of a synergistic combination (b1)+(b2), where:

the amount of the surfactant mixture lies within the 1.2 to 3% range;

the (b1)/(b2) weight ratio lies within the 0.8 to 1.2 range.

The procedure for implementing the present invention, suitable for achieving contact angle values as low as those ranging from 25 to 27°, which gives the most effective results, is that (procedure 5) involving the use of the synergistic combination (a1)+(b2) defined above in procedure 3.

As specific examples of such a combination according to procedure 5, mention may especially be made of:

the synergistic combination (a1)+(b2), where:
(a1) is the surfactant TA1,
(b2) is the surfactant TA3,
the amount of the surfactant mixture is equal to 2% and the (a1)/(b2) weight ratio is equal to 1.6;

the synergistic combination (a1)+(b2), where:
(a1) is the surfactant TA1,
(b2) is the surfactant TA3,
the amount of the surfactant mixture is equal to 1.75% and the (a1)/(b2) weight ratio is equal to 0.75; and the synergistic combination (a1)+(b2), where:
(a1) is the surfactant TA1,
(b2) is the surfactant TA3,
the amount of the surfactant mixture is equal to 1.75% and the (a1)/(b2) weight ratio is equal to 1.33; and the synergistic combination (a1)+(b2), where:
(a1) is the surfactant TA1,
(b2) is the surfactant TA3,
the amount of the surfactant mixture is equal to 1.875% and
the (a1)/(b2) weight ratio is equal to 1.15.

It is apparent from the foregoing that the POS I composition comprises the following constituents:

(1) at least one POS composition carrying Si-alkenyl functional groups which are capable of reacting by addition reactions with the Si—H crosslinking functional groups of a POS (2) composition;

(2) at least one POS composition carrying Si—H functional groups which are capable of reacting with the Si-alkenyl functional groups of the POS (1) composition;

(3) optionally, at least one unreactive POS composition, differing from the POS (1) and (2) compositions, which can be used as a diluent;

(4) a catalyst for catalyzing the polyaddition reactions; and (5) a particulate reinforcing mineral filler.

With regard to the POS(1) compositions, these are polyorganosiloxanes which have, per molecule, at least two $C_2$–$C_6$ alkenyl groups linked to the silicon, these groups being located in the chain and/or at one or both chain ends.

More specifically, the POS composition comprises:
(i) siloxyl units of formula:

$$T_a Z_b SiO_{\frac{4-(a+b)}{2}} \quad (1.1)$$

in which:
T is a $C_2$–$C_6$ alkenyl group, preferably vinyl or allyl;
Z is a monovalent hydrocarbon group, not having any action unfavourable to the activity of the catalyst and preferably chosen from alkyl groups having from 1 to 8 carbon atoms inclusive, optionally substituted with at least one halogen atom, advantageously chosen from methyl, ethyl, propyl and 3,3,3-trifluoropropyl groups, and from aryl groups and, advantageously, from xylyl, tolyl and phenyl radicals;
a is 1 or 2, b is 0, 1 or 2 and a+b is between 1 and 3, preferably between 2 and 3; and
(2i) optionally other siloxyl units of formula:

$$Z_c SiO_{\frac{4-c}{2}} \quad (1.2)$$

in which Z has the same meaning as above and c has a value of between 0 and 3, preferably between 2 and 3.

It is advantageous for this POS composition to have a viscosity of between 200 and 20 000 mPa.s and preferably between 500 and 5000 mPa.s.

Of course, in the case of a mixture of several oils (1) of different viscosity, it is the viscosity of the mixture which is taken into account.

All the viscosities involved here correspond to a dynamic viscosity parameter measured, in a manner known per se, at 25° C.

The POS(1) composition may be only formed from units of formula (1.1) or it may also contain units of formula (1.2). Likewise, it may have a linear, branched, cyclic or network structure.

Z is generally chosen from methyl, ethyl and phenyl radicals, at least 60 mol % (or 60% by number) of the radicals Z being methyl radicals.

Examples of siloxyl units of formula (1.1) are vinyldimethylsiloxyl, vinylphenylmethylsiloxyl, vinylmethylsiloxyl and vinylsiloxyl units.

Examples of siloxyl units of formula (1.2) are $SiO_{4/2}$, dimethylsiloxyl, methylphenylsiloxyl, diphenylsiloxyl, methylsiloxyl and phenylsiloxyl units.

Examples of POS(1) compositions are linear and cyclic compounds such as: dimethylvinylsilyl-terminated dimethylpolysiloxanes, trimethylsilyl-terminated (methylvinyl)(dimethyl)polysiloxane copolymers, dimethylvinylsilyl-terminated (methylvinyl) (dimethyl)polysiloxane copolymers; cyclic methylvinylpolysiloxanes.

With regard to the POS(2) compositions, these are polyorganosiloxanes which have, per molecule, at least two hydrogen atoms linked to the silicon, these Si—H groups being located in the chain and/or at a chain end.

A person skilled in the art knows well that, when the POS(1) composition has 2 alkenyl groups per molecule, the POS(2) composition must preferably have at least 3 hydrogen atoms per molecule. Conversely, when the POS(2) composition has 2 hydrogen atoms per molecule, the POS(1) composition preferably has at least 3 alkenyl groups per molecule.

The POS(2) composition is more specifically a polyorganosiloxane comprising:

(i) siloxyl units of formula:

$$H_d L_e SiO_{\frac{4-(d+e)}{2}} \quad (2.1)$$

in which:

L is a monovalent hydrocarbon group, having no action unfavourable to the activity of the catalyst and chosen, preferably, from alkyl groups having from 1 to 8 carbon atoms inclusive, optionally substituted with at least one halogen atom, advantageously chosen from methyl, ethyl, propyl and 3,3,3-trifluoropropyl groups, and from aryl groups and, advantageously, from xylyl, tolyl and phenyl radicals;

d is 1 or 2, e is 0, 1 or 2 and d+e has a value of between 1 and 3, preferably between 2 and 3; and (2i) composition optionally other siloxyl units of average formula:

$$L_g SiO_{\frac{4-g}{2}} \quad (2.2)$$

in which L has the same meaning as above and g has a value of between 0 and 3, preferably between 2 and 3.

The dynamic viscosity of this polyorganosiloxane (2) is at least equal to 10 mPa.s and is preferably between 20 and 1000 mPa.s.

The POS(2) composition may be only formed from units of formula (2.1) or it may also include units of formula (2.2).

The polyorganosiloxane (2) may have a linear, branched, cyclic or network structure.

The group L has the same meaning as the group Z above. Examples of units of formula (2.1) are:

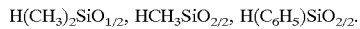

$$H(CH_3)_2SiO_{1/2}, HCH_3SiO_{2/2}, H(C_6H_5)SiO_{2/2}.$$

The examples of units of formula (2.2) are the same as those given above for the units of formula (1.2).

Examples of POS(2) compositions are linear and cyclic compounds such as:

hydrogenodimethylsilyl-terminated dimethylpolysiloxanes;

trimethylsilyl-terminated (dimethyl)(hydrogenomethyl) polysiloxane copolymers;

hydrogenodimethylsilyl-terminated (dimethyl)(hydrogenomethyl)polysiloxane copolymers;

trimethylsilyl-terminated hydrogenomethylpolysiloxanes; and cyclic hydrogenomethylpolysiloxanes.

The ratio of the number of hydrogen atoms linked to the silicon in the POS(2) composition to the total number of groups with alkenyl unsaturation in the POS(1) composition is between 0.4 and 10, preferably between 1 and 5.

With regard to the unreactive POS(3) compositions, usable as diluents, these may advantageously be a polydiorganosiloxane such as a trialkylsilyl-terminated polydialkylorganosiloxane; trimethylsilyl-terminated polydimethylsiloxanes are preferred. The dynamic viscosity at 25° C. of the POS(3) compositions is between 10 and 5000 mPa.s and preferably between 20 and 1000 mPa.s. These POS(3) compositions, when these are employed, are present in an amount of 10 to 120 parts by weight, and preferably 20 to 100 parts by weight, per 100 parts of the POS(1) and (2) compositions.

With regard to the catalysts (4) for catalysing the polyaddition reactions, these are well known to those skilled in the art.

It is preferred to use platinum and rhodium compounds. In particular, it is possible to use complexes of platinum and of an organic product described in patents U.S. Pat. Nos. 3,159,601, 3,159,602 and 3,220,972 and European patents EP-A-0 057 459, EP-A-0 188 978 and EP-A-0 190 530 and the complexes of platinum and of vinyl organosiloxanes described in patents U.S. Pat. Nos. 3,419,593, 3,715,334, 3,377,432 and 3,814,730. The catalyst more especially preferred is based on platinum. In this case, the amount by weight of catalyst (4), calculated by weight of platinum metal, is generally between 2 and 400 ppm, preferably between 5 and 100 ppm, these being based on the total weight of the POS(1) and (2) compositions.

With regard to the particulate reinforcing mineral filler (5), the filler normally used consists of a silicious filler. As silicious fillers that can be used, all precipitated or pyrogenic silicas known to those skilled in the art are suitable. Of course, it is also possible to use cuts of various silicas.

Preferred precipitation silicas and/or pyrogenic silicas are those having a BET specific surface area of greater than 40 m$^2$/g, and more precisely between 50 and 300 m$^2$/g. More preferably, pyrogenic silicas having the abovementioned specific surface area characteristics are used. Even more preferably, pyrogenic silicas having a BET specific surface area of between 170 and 230 m$^2$/g are used. In general, this reinforcing filler has an average particle size of less than 0.1 μm.

These silicas may be incorporated as they are or after they have been treated with organosilicon compounds normally used for this purpose. Among these compounds are methylpolysiloxanes, such as hexamethyldisiloxane, octamethyldisiloxane and octamethylcyclotetrasiloxane, methylpolysilazanes, such as hexamethyldisilazane and hexamethylcyclotrisilazane, chlorosilanes, such as dimethylchlorosilane, trimethylchlorosilane, methylvinyldichlorosilane and dimethylvinylchlorosilane, and alkoxysilanes, such as dimethyldimethoxysilane, dimethylvinylethoxysilane and trimethylmethoxysilane.

During this treatment, the silicas may increase in weight from their initial weight by up to 20%, preferably about 18%.

It should be noted that the particulate silicious mineral filler may advantageously be used in the form of the suspension obtained by treating the filler by applying the method, according to the teaching of Patent Applications WO-A-98/58997 and WO-A-00/00853, indicating a two-step treatment of the filler by a compatibilizing agent (for example chosen, with regard to the first treatment step, from a silazane, a hydroxylated siloxane, an amine or an organic acid and, with regard to the second treatment step, from silazanes) carried out in the presence of the POS (1) constituent. If such a treatment results in a basic pH, it is possible to add to the dispersion a neutralizing agent such as, for example, a weak acid. Such a particular treatment of the filler is beneficial when it is necessary for the silicone material (in the uncrosslinked state) to retain excellent fluidity.

These fillers are present in an amount from 2 to 30%, preferably from 3 to 20%, with respect to the total mass of the POS I composition.

According to one advantageous provision of the present invention, the POS composition I of the silicone material may furthermore include one or more complementary constituents chosen from the group comprising:

(6) at least one inhibitor for the polyaddition reactions;
(7) a semi-reinforcing or bulking filler;
(8) one or more colouring agents and/or sweeteners and/or flavours and/or isotonic compounds;
(9) one or more biocides; and
(10) mixtures thereof.

The inhibitors (6) are well-known compounds. It is possible, in particular, to use organic amines, organic oximes, dicarboxylic acid diesters, acetylenic alcohols, acetylenic ketones, and vinylmethylcyclopolysiloxanes (see, for example, U.S. Pat. Nos. 3,445,420 and 3,989,667). Acetylenic alcohols are preferred and, in this context, ethynylcyclohexanol (ECH) is a particularly preferred inhibitor. The concentration of inhibitor(s), when such is used, is at most equal to 2000 ppm and preferably between 2 and 500 ppm with respect to the total mass of the POS(1) and (2) compositions.

With regard to the fillers (7), these generally have a particle diameter of greater than 0.1 μm and are preferably chosen from ground quartz, zirconias, calcined clays, diatomaceous earths, calcium carbonate, aluminium and/or sodium silicates, aluminas, titanium oxide and mixtures of these species. When the fillers (7) are used, they are present in the silicone material in an amount of 5 to 60% and preferably 30 to 50% by weight with respect to the total weight of the POS composition I.

As regards the colouring agent(s) (8), it is possible to use mineral and/or organic coloured pigments.

With regard to the biocidal agent (9) which may be used in the silicone material according to the invention, it should be noted that this is preferably chosen from the active-chlorine precursor group based on N-chlorinated compounds comprising:

chloramine B (sodium N-chlorobenzene sulphonamide);
chloramine T (sodium N-chloro-p-toluene sulphonamide);
dichloramine T (N,N-dichloro-p-toluene sulphonamide);
N-trichloromethylmercapto-4-cyclohexene-1,2-dicarboxylamide;
halazone (p-n-dichlorosulphonamide benzoic acid);
N-chlorosuccinimide;
trichloromelamine;
chloroazodin

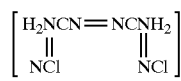

N-chloro derivatives of cyanuric acids, preferably trichloroisocyanuric acid and/or sodium dichloroisocyanuric dihydrate;
N-chlorohydantoins, preferably 1-bromo-3-chloro-5,5'-dimethylhydantoin or 1,3-dichloro-5,5'-dimethylhydantoin;
and mixtures thereof.

This group of antiseptics corresponds substantially to the N-chloramine family which comprises derivatives of amines in which one or two of the valences of the trivalent nitrogen are substituted with chlorine. In the presence of water, the N-chloramines produce hypochlorous acid HClO or salts of this acid, such as NaClO. HClO and NaClO are active chlorinated derivatives endowed with a high bactericidal capacity, which may be exploited within the context of the silicone material according to the invention (this is particularly the case when the said material is intended for taking dental impressions in the mouth).

Advantageously, the biocidal agent (9) may be combined with at least one antiseptic auxiliary agent different from the antiseptics which work by releasing chlorine and preferably chosen from the group of formulations comprising one or more quaternary ammoniums (for example, benzalkonium chloride) and optionally at least one sequestering activator, preferably selected from metal ion complexing agents (for example, ethylenediaminetetraacetic acid or EDTA)

The concentration of biocidal agent(s), when such are used, is at most equal to 1%, preferably at most equal to 0.8% and even more preferably between 0.001 and 0.5% by weight with respect to the total mass of the silicone material [I+II combined].

The present invention also relates, according to a second subject-matter, to a process for preparing the silicone material I+II as described above. This process is characterized in that it essentially consists in mixing the following ingredients:

(A) one or more POS(1) compositions as defined above;
(B) one or more POS(2) compositions as defined above;
(C) optionally, one or more POS(3) compositions as defined above;
(D) a catalyst (4) for catalysing the polyaddition reactions;
(E) a reinforcing mineral filler as defined above;
(F) optionally, one or more inhibitors (6) as defined above;
(G) optionally, a semi-reinforcing or bulking filler (7) as defined above;
(H) optionally, one or more agents (8);
(I) optionally, one or more biocidal agents (9); and
(J) one or more surfactants II as defined above.

This mixture is made in a conventional manner using suitable technical means known to those skilled in the art.

According to one advantageous arrangement, it is preferable for the ingredient (G) to be necessarily present.

According to a beneficial variant of this process:
the silicone material is produced in the form of a system based on two components A and B intended to be brought into contact with each other in order to produce an elastomer crosslinked by polyaddition reactions between the POS(1) and (2) compositions; and
measures are taken to ensure that only one of the components A and B contains the catalyst (D) and possibly one or other of the POS(1) and (2) compositions.

According to a preferred method of implementing the variant of the process described above, measures are taken to ensure that the surfactant or the surfactant mixture is introduced into the component A or B which does not contain the catalyst (D).

The subject of the present invention is also the use of the silicone material I+II, as described above, for taking impressions, for example dental impressions. This use, in a preferred method of implementation, consists in taking measures to ensure that the crosslinking of the silicone elastomer is initiated by mixing the components A and B together, in taking the impression and in allowing the crosslinking to continue until the elastomer is sufficiently crosslinked and sufficiently hard.

According to another embodiment, the silicone material I+II as described above is intended for the manufacture of moulded parts, other than duplicates in dental applications, which are capable of developing a pronounced hydrophilic and/or antistatic character on the surface; the said moulded parts are manufactured using, for example, casting-type moulding processes or injection moulding processes. It should be noted that, in the case of casting-type moulding processes, in which it is preferable for the silicone material to be able to retain excellent fluidity in the uncrosslinked state, it is then advantageous to use the two-step particular treatment of the silicious filler with a compatibilizing agent, mentioned above in the definition of the particulate reinforcing mineral filler (5).

As specific examples of moulded parts, other than duplicates in dental applications, mention may especially be made of pads such as those used in pad printing techniques and rollers of photocopiers.

Within the context of this other method of use, the silicone material I+II, as described above, is particularly intended for the manufacture of pads such as those used in pad printing techniques, in which it is beneficial to be able to have available a material having high mechanical properties, the surface energy of which may be modulated by adding one or more surfactants, while maintaining the level of fluidity necessary for manufacturing pads by moulding preferably by casting. This other particular use, in a preferred method of implementation, consists in taking measures to ensure that the crosslinking of the silicone elastomer is initiated by mixing the components A and B together, in forming, by moulding an object having the shape of the desired pad and in allowing the crosslinking to continue until the elastomer is sufficiently crosslinked and sufficiently hard.

Although the crosslinking by polyaddition reactions between the POS(1) and (2) compositions can be initiated and already developed at a temperature close to room temperature (23° C.), it is also possible to carry out the crosslinking thermally (for example by heating to a temperature ranging from 60° C. to 110° C.) and/or by electromagnetic radiation (electron beam) and/or by infrared radiation.

A clearer understanding of the invention will be gained from the examples which follow and which describes the preparation of a silicone material according to the invention, together with its evaluation in terms of fluidity, hydrophilicity and mechanical properties.

EXAMPLES

Examples 1 to 26 and Control Tests 1 to 5

1. List of the Raw Materials Used:
   1.1 Component A of the bicomponent:
   POS (1): polydimethylsiloxane oil terminated at each of the chain ends by a $(CH_3)_2ViSiO_{1/2}$ unit having a viscosity of 600 mPa.s and containing about 0.014 vinyl (Vi) functional groups in 100 g of oil;

catalyst (4): platinum (0) complexed by divinyltetramethyldisiloxane: what is used is a solution in divinyltetramethyldisiloxane of a platinum complex containing approximately 11% by weight of platinum (0) with a ligand (called Karstedt's catalyst);

filler (5): pyrogenic silica, sold under the name AEROSIL R 972, treated with octamethylcyclotetrasiloxane;

filler (7): ground quartz having a mean particle size of 10 μm, sold under the name SICRON SA 600; and white colouring base (8): $TiO_2$ in dispersion (60% by weight of $TiO_2$) dispersed in a POS (1) oil fraction.

1.2 Component B of the bicomponent:
   POS (1): cf. component A;
   POS (1'): polydimethylsiloxane oil terminated at each of the chain ends with a $(CH_3)_2ViSiO_{1/2}$ unit, having a viscosity of 3500 mPa.s and containing approximately 0.0074 vinyl (Vi) functional groups in 100 g of oil;

POS (2): poly(dimethyl)(hydrogenomethyl)siloxane oil terminated at each of the chain ends with a $(CH_3)_2HSiO_{1/2}$ unit, having a viscosity of 30 mPa.s and containing approximately 0.25 SiH functional groups in 100 g of oil;

filler (5): cf. component A;
   filler (7): cf. component B;
   yellow colouring base (8): mixture of 30% by weight of quinoline yellow in 70% by weight of POS (1') oil; and wetting agent II: cf. legends (1) to (6) appended to Tables 1, 2 and 3 given below.

2. Constitution of Components A and B of the Bicomponents Tested:

|  | Component A | Component B |
| --- | --- | --- |
| POS I composition: |  |  |
| POS (1) | 49.5 (*) | 38.8 |
| POS (1') | — | 2.7 |
| POS (2) | — | 9.1 |
| Platinum (0) with ligand (4) | 0.015 | — |
| Divinyltetramethyl-disiloxane (4) | 0.035 | — |
| Filler (5) | 3.75 | 3.6 |
| Filler (7) | 45.7 | 44.6 |
| $TiO_2$ (8) | 1.0 | — |
| quinoline yellow (8) | — | 1.2 |
| Surfactant(s) II | — | cf. Tables 1, 2 and 3 given below (**) |

(*): parts by weight: the sum of the constituents of the POS I composition is equal to 100 parts;
(**): the amount of surfactant(s) introduced into the component B of the bicomponent corresponds to the values indicated in the Tables (on the % by weight in A + B line) multiplied by a factor of 2.

3. Preparation of the Compositions:
   3.1 Component A:
   The following constituents were introduced at 23° C. into a planetary mixer: POS (1), filler (7), filler (5) and colouring base (8); all this was homogenized by stirring at 400 revolutions/minute for 2 hours.

The stirring was then stopped and Karstedt's catalyst (4) then added; further homogenization by stirring at 400 revolutions/minute for 10 minutes.

Next, without stopping the stirring, the mixture was degassed at 23° C., working under a reduced pressure of 266×10² Pa for 10 minutes.

3.2 Component B:

The following steps were carried out in the above mixer:

Introduction of the POS (1) compositions, filler (7), filler (5) and colouring base (8) based on quinoline yellow and POS (1') oil and homogenization at 23° C. with stirring at 50 revolutions/minute for 2 hours.

The stirring was stopped and POS (2) and surfactant(s) were added; further homogenization by stirring at 50 revolutions/minute for 1 hour.

Finally, the mixture was degassed as indicated above in the case of component A, but while stirring at 50 revolutions/minute.

3.3 Bicomponent A+B:

The silicone material according to the invention was obtained by mixing, at a room temperature of 23° C., 50 parts by weight of the component A with 50 parts by weight of the component B. The crosslinking of each bicomponent was carried out at a room temperature of 23° C., after producing the A+B mixture.

4. Results:

These are given in Tables 1, 2 and 3 which follow.

TABLE 1

|  | Control 1 | Control 2 | Ex. 1 | Ex. 2 | Ex. 3 | Control 3 | Ex. 4 | Ex. 5 | Ex. 6 | Control 4 | Ex. 7 |
|---|---|---|---|---|---|---|---|---|---|---|---|
| Surfactant(s) | | | | | | | | | | | |
| nature: (1 to 6) | — | TA6 | TA1 | TA1 | TA1 + TA2 | TA2 | TA1 + TA3 | TA1 + TA3 | TA1 + TA4 | TA4 | TA1 + TA5 |
| % by weight of the surfactant(s) in A + B: (7) | — | 2 | 2 | 3 | 2 | 2 | 2 | 2 | 2 | 2 | 2 |
| weight ratio of the surfactants (8) | — | — | — | — | 1 | — | 1 | 1.6 | 1 | — | 1 |
| Crosslinking kinetics | | | | | | | | | | | |
| working time: | 1'15" | 1'30" | 2'35" | 2'15" | 2'35" | 2'25" | 2'35" | 2'20" | 2'10" | 2'15" | 2'30" |
| setting time: (9) | 2'15" | 2'22" | 4'20" | 3'10" | 3'35" | 3'55" | 4'20" | 4'10" | 3'55" | 3'55" | 4'20" |
| Shore A hardness | | | | | | | | | | | |
| 8 min: | 49 | 49 | 48 | 49 | 46 | 46 | 47 | 47 | 49 | 47 | 49 |
| 24 hours: (10) | 50 | 51 | 49 | 50 | 48 | 49 | 49 | 49 | 51 | 50 | 49 |
| Contact angle (11) | 105° | 61.4° | 38° | 36.2° | 29° | 41.7° | 32.5° | 25° | 33° | 45° | 30.5° |

TABLE 2

|  | Ex. 8 | Control 5 | Ex. 9 | Ex. 10 | Ex. 11 | Ex. 12 | Ex. 13 | Ex. 14 | Ex. 15 | Ex. 16 | Ex. 17 |
|---|---|---|---|---|---|---|---|---|---|---|---|
| Surfactant(s) | | | | | | | | | | | |
| nature: (1 to 6) | TA2 + TA3 | TA3 | TA1 + TA3 | TA1 + TA3 | TA1 + TA3 | TA1 + TA3 | TA1 + TA3 | TA1 + TA3 | TA1 + TA3 | TA1 + TA3 | TA1 + TA3 |
| % by weight of the surfactant(s) in A + B: (7) | 2 | 2 | 1.25 | 1.25 | 1.375 | 1.375 | 1.5 | 1.5 | 1.6 | 1.6 | 1.75 |
| weight ratio of the surfactants (8) | 1 | — | 0.25 | 4 | 0.375 | 2.65 | 0.5 | 2 | 0.62 | 1.6 | 0.75 |
| Crosslinking kinetics | | | | | | | | | | | |
| working time: | 2'30" | 2'35" | 2'20" | 2'20" | 2'25" | 2'20" | 2'25" | 2'20" | 2'35" | 2'20" | 2'30" |
| setting time: (9) | 4'25" | 4'35" | 4' | 4' | 4'05" | 4' | 4' | 3'55" | 4'35" | 4' | 4'30" |
| Shore A hardness | | | | | | | | | | | |
| 8 min: | 47 | 48 | 48 | 48 | 48 | 47 | 48 | 47 | 47 | 47 | 48 |
| 24 hours: (10) | 49 | 49 | 49 | 49 | 49 | 49 | 50 | 49 | 48 | 49 | 49 |
| Contact angle (11) | 27° | 48.1° | 34.5° | 33° | 30.5° | 34° | 30° | 30° | 28.5° | 29° | 25.5° |

TABLE 3

|  | Ex. 18 | Ex. 19 | Ex. 20 | Ex. 21 | Ex. 22 | Ex. 4 | Ex. 5 | Ex. 23 | Ex. 24 | Ex. 25 | Ex. 26 |
|---|---|---|---|---|---|---|---|---|---|---|---|
| Surfactant(s) | | | | | | | | | | | |
| nature: (1 to 6) | TA1 + TA3 | TA1 + TA3 | TA1 + TA3 | TA1 + TA3 | TA1 + TA3 | TA1 + TA3 | TA1 + TA3 | TA1 + TA3 | TA1 + TA3 | TA1 + TA3 | TA1 + TA3 |
| % by weight of the surfactant(s) in A + B: (7) | 1.75 | 1.875 | 1.875 | 2 | 2 | 2 | 2 | 2 | 2 | 2 | 2 |
| weight ratio of the surfactants (8) | 1.33 | 0.875 | 1.15 | 0.14 | 0.6 | 1 | 1.6 | 2 | 3 | 4 | 7 |

TABLE 3-continued

|  | Ex. 18 | Ex. 19 | Ex. 20 | Ex. 21 | Ex. 22 | Ex. 4 | Ex. 5 | Ex. 23 | Ex. 24 | Ex. 25 | Ex. 26 |
|---|---|---|---|---|---|---|---|---|---|---|---|
| Crosslinking kinetics | | | | | | | | | | | |
| working time: | 2'25" | 2'35" | 2'30" | 2'44" | 2'35" | 2'35" | 2'30" | 2'30" | 2'35" | 2'35" | 2'35" |
| setting time: (9) | 4'30" | 4'20" | 4'10" | 4'25" | 4'15" | 4'20" | 4'10" | 4'10" | 4'10" | 4'20" | 4'20" |
| Shore A hardness | | | | | | | | | | | |
| 8 min: | 48 | 47 | 48 | 48 | 48 | 48 | 48 | 48 | 48 | 48 | 48 |
| 24 hours: (10) | 49 | 49 | 49 | 49 | 49 | 49 | 49 | 49 | 49 | 49 | 49 |
| Contact angle (11) | 25.5° | 29° | 25.7° | 31° | 33.5° | 32.5° | 25° | 29.3° | 29.5° | 29.6° | 28° |

Legends for Tables 1, 2 and 3:

(1) TA1: LINCOL PE 400 ML;
(2) TA2: RHODASURF ROX;
(3) TA3: TEGOPREN LP 111;
(4) TA4: ANTAROX FM 33;
(5) TA5: RHODASURF OT/2;
(6) TA6: TEGOPREN 5863 (polyorganosiloxane having polyether functional groups);
(7) % by weight in A+B: that is to say the % by weight in the sum of components A and B of the bicomponent in which the component B is considered without taking into account the surfactant(s);
(8) Weight ratio: this is the TA1/co-surfactant (TA2, TA3, TA4 or TA5) weight ratio; or the TA2/TA3 weight ratio;
(9) The crosslinking kinetics were determined manually. The following times were determined:
  working time: this corresponds to the time during which the mixture of the 2 components A and B retains fluid behaviour, allowing it to be applied to the models to be reproduced; after this time, the mixture acquires the characteristics of an elastomer;
  setting time: this corresponds to the time, at 23° C., after which the curing is completed; the mixture is then dry to the touch and the impression, for example dental impression, can be removed from the mouth;
(10) The Shore A hardness is measured, firstly, 8 minutes after producing the mixture of components A and B (that is to say after 8 minutes of crosslinking) and secondly 24 hours after producing the mixture of the 2 components A and B (that is to say after 24 hours of crosslinking), in an atmosphere controlled at 23° C. and 50% relative humidity, the procedure being carried out according to the indications in the DIN 53505 standard using a durometer sold under the name ZWICK 3140.H04 and with pins 6 mm in thickness; and
(11) Contact angles: The hydrophilicity is measured 10 minutes after the end of crosslinking of the silicone material; the said end of crosslinking is obtained, in general, 15 minutes after the 2 components A and B have been mixed. The method consists in depositing a drop of water about 10 to 60 mm³ in volume onto the surface of a film, based on the crosslinked silicone elastomer, and in measuring the contact angle θ using a camera (with image magnification) and a goniometer consisting of the instrument sold under the name OLYMPUS DMS 300. The angles are measured 3 minutes after depositing the drop. The values indicated are averages of 3 measurements. The measurements are carried out in an atmosphere controlled to 23° C. and 50% relative humidity. The crosslinked silicone elastomer films, having dimensions of 7 cm×3 cm×0.2 cm, are prepared by spreading out a bead of silicone material while still fluid using a doctor blade and the material is left to crosslink right to its completion.

Examples 5, 8, 17, 18 and 20 reported above clearly show that the present invention makes it possible to obtain a silicone material having, on the one hand, a very high pronounced level of hydrophilicity by obtaining contact angles as low as those ranging from 25 to 27° and better still from 25° to a value of less than 26°, and, on the other hand, excellent pronounced mechanical properties, especially by obtaining Shore A hardness values at 8 minutes or at 24 hours lying within the 45–55 range.

The invention claimed is:

1. Silicone material which comprises the following constituents:
  I. a POS composition crosslinkable by polyaddition reactions comprising:
    (1) at least one POS composition carrying Si-alkenyl functional groups which are capable of reacting by addition reactions with the Si—H crosslinking functional groups of a POS(2) composition,
    (2) at least one POS composition carrying Si—H functional groups which are capable of reacting with the Si-alkenyl functional groups of the POS(I) composition,
    (3) optionally, at least one unreactive POS composition, differing from the POS(1) and POS(2) compositions, which can be used as a diluent,
    (4) a catalyst for catalysing the polyaddition reactions,
    (5) a particulate reinforcing mineral filler;
  II. a wetting agent comprising one or a mixture of more surfactants allowing the surface of the silicone material to be given a pronounced hydrophilic character, both before and after crosslinking;
  wherein the wetting agent II is selected from the group consisting of:
    (a) at least one nonionic surfactant consisting of an ester obtained by esterification of a saturated monocarboxylic acid having a $C_{10}$–$C_{14}$ linear or branched chain by a poly(oxyalkylene)glycol containing a number of alkoxylated units such that the molar mass $M_w$ of the ester lies within the 400 to 800 g/mol range, the HLB of the said surfactant or of the mixture of surfactants ranging from 6 to 14;
    a synergistic combination (a)+(b), where (b) denotes at least one nonionic surfactant consisting of a polyalkoxylated saturated aliphatic alcohol having a $C_5$–$C_{16}$ linear or branched chain, containing a number of alkoxylated units such that the molar mass $M_w$ of the polyalkoxylated alcohol lies within the 200 to 1400 g/mol range, the HLB of the said surfactant (b) or of the mixture of surfactants (b) ranging from 6 to 16; and a synergistic combination (b1)+(b2), where (b1) denotes at least one nonionic surfactant consisting of a polyethoxylated saturated aliphatic alcohol having a $C_{10}$–$C_{16}$ linear or branched chain, containing from 6 to 10 ethylene oxide (EO) units, the HLB of the said surfactant (b1) or of the mixture of surfactants (b1) ranging from 12 to 16, and (b2) denotes at least one nonionic surfactant consisting of a polyalkoxylated saturated aliphatic alcohol having a $C_6$–$C_{13}$ linear or branched chain, containing a number of ethylene oxide (EO) and propylene oxide (PO) units such that the molar mass $M_w$ of the polyalkoxylated alcohol lies within the 500 to 1200 g/mol range, the HLB of the said surfactant (b2) or of the mixture of surfactants (b2) ranging from 6 to 16.

2. Material according to claim 1, the amount of surfactant or that of a mixture of surfactants, expressed in % by weight with respect to the total mass of the POS I composition, is equal to or greater than 1%.

3. Material according to claim 1 comprising a wetting agent selected from the group consisting of:
   (a1) at least one nonionic surfactant consisting of an ester obtained by esterification of a saturated monocarboxylic acid having a $C_{10}$–$C_{14}$ linear or branched chain by a poly(oxyalkylene)glycol containing from 7 to 11 EO and/or PO units, the HLB of said surfactant or of the mixture of surfactants ranging from 10 to 14;
   a synergistic combination (a1)+(b1);
   a synergistic combination (a1)+(b2);
   a synergistic combination (a1)+(b3),
   where (b3) denotes at least one nonionic surfactant comprising a polyethoxylated saturated aliphatic alcohol having a $C_{10}$–$C_{14}$ linear or branched chain, comprising from 1 to 4 EO units, the HLB of the said surfactant (b3) or of the mixture of surfactants (b3) ranging from 6 to 10; and
   a synergistic combination (b1)+(b2).

4. Material according to claim 3, wherein to achieve contact angles equal to or less than 30°, the material further comprises a wetting agent selected from the group consisting of:
   a synergistic combination (a1)+(b1);
   a synergistic combination (a1)+(b2); and
   a synergistic combination (b1)+(b2);
   where:
   the amount of the surfactant mixture lies within the 1.2 to 3% by weight range;
   the (a1)/(b1) weight ratio lies within the 0.5 to 1.5 range;
   the (a1)/(b2) weight ratio lies within the 0.5 to 7 range and wherein:
   (i) when the (a1)/(b1) weight ratio lies within the 0.5 to 1.2 range, then the amount of the surfactant mixture is less than 1.8% by weight; (2i) when the (a1)/(b2) weight ratio lies within the 3 to 7 range, then the amount of the surfactant mixture is equal to or greater than 1.8% by weight; and (3i) when the (a1)/(b2) weight ratio lies within the range going from a value greater than 1.2 to a value less than 3, then the amount of the surfactant mixture is equal to any value taken within the 1.2 to 3% by weight range given above;
   the (b1)/(b2) weight ratio lies within the 0.5 to 1.5 range.

5. Material according to claim 4, wherein, to achieve contact angle values as low as those ranging from 25 to 27°, the material further comprises a synergistic combination (a1)+(b2), where:
   the amount of the surfactant mixture lies within the 1.2 to 3% by weight range;
   the (a1)/(b2) weight ratio lies within the 0.7 to 1.7 range, and wherein:
   (i) when the (a1)/(b2) weight ratio lies within the 0.7 to 1 range, then the amount of the surfactant mixture is less than 1.8% by weight; (2i) when the (a1)/(b2) weight ratio lies within the 1.5 to 1.7 range, then the amount of the surfactant mixture is equal to or greater than 1.8% by weight; and (3i) when the (a1)/(b2) weight ratio lies within the range going from a value greater than 1 to a value less than 1.5, then the amount of the surfactant mixture is equal to any value taken within the 1.2 to 3% by weight range given above.

6. Material according to claim 4, wherein to achieve contact angle values as low as those ranging from 25 to 27°, the material further comprises a wetting agent comprising a synergistic combination (b1)+(b2), where:
   the amount of the surfactant mixture lies within the 1.2 to 3% by weight range;
   the (b1)/(b2) weight ratio lies within the 0.8 to 1.2 range.

7. Material according to claim 1, wherein the POS(1) composition comprises:
   (i) siloxyl units of formula:

$$T_a Z_b SiO_{\frac{4-(a+b)}{2}} \qquad 1.1$$

in which:
   T is a $C_2$–$C_6$ alkenyl group;
   Z is a monovalent hydrocarbon group, not having any action unfavorable to the activity of the catalyst and selected from alkyl groups having from 1 to 8 carbon atoms inclusive, optionally substituted with at least one halogen atom, and from aryl groups;
   a is 1 or 2, b is 0, 1 or 2 and a+b is between 1 and 3; and
   (2i) optionally other siloxyl units of formula:

$$Z_c SiO_{\frac{4-c}{2}} \qquad (1.2)$$

in which Z has the same meaning as above and c has a value of between 0 and 3.

8. Material according to claim 1, wherein the POS(2) composition comprises:
   (i) siloxyl units of formula:

$$H_d L_e SiO_{\frac{4-(d+e)}{2}} \qquad (2.1)$$

in which:
   L is a monovalent hydrocarbon group, having no action unfavorable to the activity of the catalyst and selected from alkyl groups having from 1 to 8 carbon atoms inclusive, optionally substituted with at least one halogen atom, and from aryl groups;
   d is 1 or 2, e is 0, 1 or 2 and d+e has a value of between 1 and 3; and
   (2i) optionally other siloxyl units of average formula:

$$L_g SiO_{\frac{4-g}{2}} \qquad (2.2)$$

in which L has the same meaning as above and g has a value of between 0 and 3.

9. Material according to claim 1, further comprising one or more complementary constituents selected from the group consisting of:
(6) at least one inhibitor for the polyaddition reactions;
(7) a semi-reinforcing or bulking filler;
(8) one or more coloring agents and/or sweeteners and/or flavors and/or isotonic compounds;
(9) one or more biocides; and
(10) mixtures thereof.

10. Material according to claim 9, comprising the following points:
the silicone material is produced in the form of a system based on two components A and B intended to be brought into contact with each other in order to produce an elastomer crosslinked by polyaddition reactions between the POS(1) and (2) compositions; and
measures are taken to ensure that only one of the components A and B contains the catalyst (D) and optionally one or other of the POS(1) and (2) compositions.

11. A method for taking impressions, the method comprising takinci an impression using the silicone material according to claim 1.

12. The method according to claim 11, further comprising taking measures to ensure that the crosslinking of the silicone elastomer is initiated by mixing the components A and B together, when taking the impression and in allowing the crosslinking to continue until the elastomer is sufficiently crosslinked and sufficiently hard.

13. A method for the manufacture of molded parts, other than duplicates in dental applications, which are capable of developing a pronounced hydrophilic and/or antistatic character on the surface, the method comprising manufacturing a molded part using the silicone material according to claim 1.

14. The method according to claim 13, wherein the molded parts, other than duplicates in dental applications, are pads, such as those used in pad printing techniques, and rollers of photocopiers.

15. The method according to claim 14, further comprising taking measures to ensure that the crosslinking of the silicone elastomer is initiated by mixing the components A and B together, when forming, by molding, an object having the shape of the desired pad and allowing the crosslinking to continue until the elastomer is sufficiently crosslinked and sufficiently hard.

16. Process for preparing a silicone material I+II according to claim 1, comprising mixing the following ingredients:
(A) one or more POS(1) compositions;
(B) one or more POS(2) compositions;
(C) optionally, one or more POS(3) compositions;
(D) a catalyst (4) for catalysing the polyaddition reactions;
(E) a reinforcing mineral filler;
(F) optionally, one or more inhibitors (6);
(G) optionally, a semi-reinforcing or bulking filler (7);
(H) optionally, one or more agents (8);
(I) optionally, one or more biocidal agents (9); and
(J) one or more wetting agent II.

17. Crosslinkable silicone material made of a silicone elastomer by polyaddition reactions, wherein the material is obtained by the process according to claim 16, and has the following properties measured after crosslinking in an atmosphere controlled to 23° C. and 50% relative humidity:
a pronounced hydrophilic character indicated by a value of the drop angle $\theta$ equal to or less than 27°; and
a Shore A hardness at 8 minutes or at 24 hours lying within the 45–55 range.

18. A method for taking impressions, the method comprising taking an impression using the material according to claim 17.

19. A method for the manufacture of molded parts, other than duplicates in dental applications, which are capable of developing a pronounced hydrophilic and/or antistatic character on the surface, the method comprising manufacturing a molded part using the material according to claim 17.

20. The method according to claim 19, wherein the molded parts, other than duplicates in dental applications, are pads.

* * * * *